United States Patent [19]

Peterson et al.

[11] 4,414,858
[45] Nov. 15, 1983

[54] STEAM TURBINE FLUID SAMPLING APPARATUS

[75] Inventors: Steven H. Peterson, Murrysville; David F. Pensenstadler, North Huntingdon, both of Pa.

[73] Assignee: Westinghouse Electric Corp., Pittsburgh, Pa.

[21] Appl. No.: 360,739

[22] Filed: Mar. 22, 1982

[51] Int. Cl.³ .............................................. G01N 1/26
[52] U.S. Cl. .............................. 73/863.33; 137/625.11
[58] Field of Search ......................... 73/863.33, 863.31; 137/625.11; 364/509

[56] References Cited

U.S. PATENT DOCUMENTS

| | | | |
|---|---|---|---|
| 2,595,311 | 5/1952 | Strange et al. | 137/144 |
| 2,721,578 | 10/1955 | Pouppirt, Jr. | 137/637 X |
| 2,736,201 | 2/1956 | Ohlsen et al. | 73/863.31 X |
| 2,840,109 | 6/1958 | Wadleigh | 137/625.11 |
| 3,043,145 | 7/1962 | Hoffman | 73/23 X |
| 3,607,073 | 9/1977 | Stamm | 364/509 X |
| 3,757,583 | 9/1973 | Ludewig, Jr. | 137/625.11 X |
| 3,846,075 | 11/1974 | Cioffi | 73/863.33 X |
| 3,921,456 | 11/1975 | Newcomb, Jr. et al. | 73/23 X |
| 3,927,670 | 12/1975 | Turney et al. | 73/23.1 X |
| 4,090,392 | 5/1978 | Smith et al. | 73/863.33 |

Primary Examiner—Daniel M. Yasich
Attorney, Agent, or Firm—D. Schron

[57] ABSTRACT

Apparatus for sampling water or steam condensate in a steam turbine system includes a plurality of lines connected to receive fluid samples from various points in the system for delivering a selected sample to an analyzer through a valving arrangement. The valving arrangement and analyzer are under control of a microprocessor which has a set of stored instructions governing the random selection of which lines are to be selected for sampling. The selection may be interrupted as a result of the analysis whereas the result of abnormal fluid conditions in a particular line is determined by sensors provided in each line. The valves are of the type which provide for continuous fluid flow therethrough so that a fluid sample if selected will be provided to the analyzer and all those not selected will be returned back to the steam turbine system for reuse.

7 Claims, 4 Drawing Figures

STEAM TURBINE FLUID SAMPLING APPARATUS

BACKGROUND OF THE INVENTION

1. Field of the Invention

The invention in general relates to multi-point sampling systems, and particularly to an arrangement which automatically samples and analyzes water and steam condensate from a plurality of points in a steam turbine system.

2. Description of the Prior Art

In a steam turbine-generator power plant ultrahigh purity water is utilized in the generation of steam. The corrosive effects of impurities on turbines, boilers and other critical components in steam turbine power plants are well known and accordingly the circulating water for steam generation is maintained at a purity measured in parts per billion.

As part of the program for maintaining this high purity level it is necessary to collect representative samples of water or steam condensate from various locations in the steam turbine system so that they may be analyzed in order that corrective measures, if required, may be effected.

The present invention provides for the automatic collecting of representative samples of high purity water or steam condensate from various points in the steam turbine system.

SUMMARY OF THE INVENTION

Apparatus for sampling fluids in a steam turbine system in accordance with the present invention includes a valve arrangement which has a plurality of valves each of which may be activated in response to an applied control signal. A plurality of fluid sample lines is connected between various points in the steam turbine system and the valve arrangement. An analyzer is provided for analyzing selected fluid samples passed by the valving arrangement and all of those samples which are not selected are continuously flowing to a common drain line which is connected back to steam turbine fluid system so as to minimize loss of high purity water. A computer such as a microprocessor supplies the control signals to activated selected ones of the valves in accordance with a set of stored instructions so as to place a single one of the fluid sample lines in fluid communication with the analyzer.

Each fluid sample line includes a sensor providing an output signal to the computer whereby the sampling pattern of the fluid sample lines may be altered if the particular sensor output indicates an alarm condition. Similarly, the computer may alter the sampling sequence in response to the analyzer output if such output indicates the necessity for such alteration.

DESCRIPTION OF THE PREFERRED EMBODIMENT

Figure 1:
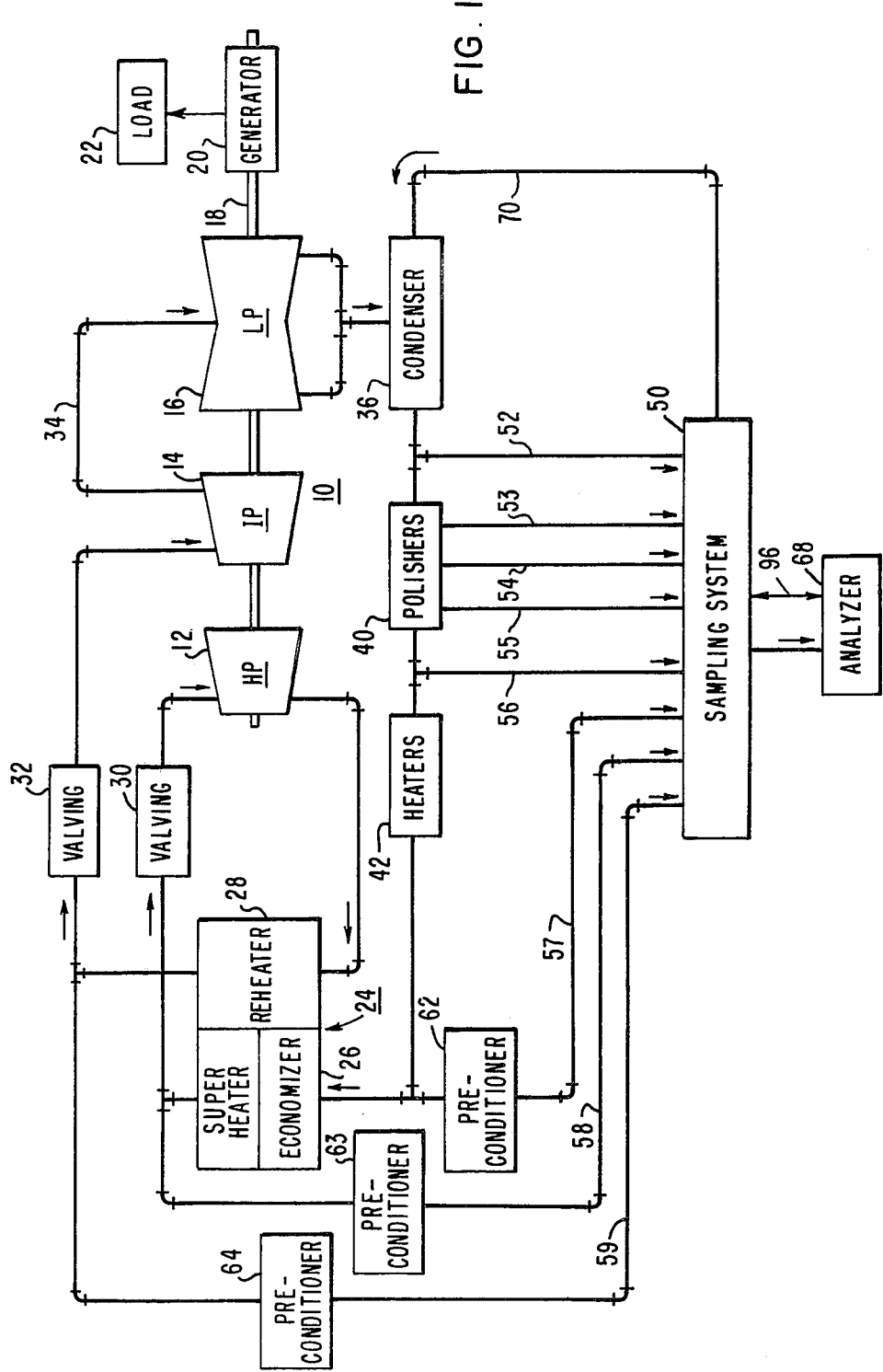
FIG. 1 illustrates a simplified diagram of a steam turbine-generator power plant.

FIG. 1 illustrates a typical steam turbine system for a power plant and includes a steam turbine arrangement 10 having a plurality of turbines in the form of high pressure turbine 12, intermediate pressure turbine 14 and low pressure turbine 16, all of which are coupled to a common shaft 18 to drive an electrical generator 20 which supplies power to a load 22.

A steam supply in the form of a boiler system 24 includes, by way of example, an input economizer section 26 and a reheater section 28. Boiler steam is provided to the turbine arrangement 10 through input valving 30 and steam exiting the high pressure turbine 12 is reheated in reheater section 28 and provided to intermediate pressure turbine 14 through valving 32. Steam exiting the intermediate pressure turbine 14 is provided by way of crossover piping 34 to the low pressure turbine 16 from which the steam is exhausted into a conventional condenser 36.

Water in the condenser is recirculated back to the boiler after chemical treatment to maintain high purity. The chemical treatment may include a plurality of polishers 40 which basically are ion exchange units designed to remove impurities. After the chemical treatment the water is heated by a series of heaters 42 and returned to the input economizer 26 of the boiler system 24.

A sampling system 50 is provided and in accordance with the present invention automatically obtains samples from various points in the steam turbine system. By way of example, fluid sample line 52 samples condensate fluid from condenser 36. Fluid sample lines 53–55 are connected to sample effluent from respective first, second and third polishers while line 56 samples the combined polisher effluent. Line 57 is connected to sample the input to the economizer 26, line 58 samples the main steam output and line 59 is cnnected to sample the hot reheat steam.

Since some of the fluid samples might be at elevated temperatures and pressures, a plurality of preconditioners are provided to reduce temperatures and pressures of the circulating fluid to manageable values. By way of example lines 57–59 contain respective preconditioners 62–64 so as to reduce the temperature and pressure of fluid at the input to the economizer, output of the boiler system, and output of the reheater, respectively.

In operation, the sampling system 50 will communicate one of the fluid sample lines to analyzing equipment 68 and will communicate all the non-selected lines to a common drain line 70 connected to supply the fluid in the fluid sample lines back to the recirculating fluid of the steam turbine system. By way of example common drain line 70 may be connected directly to condenser 36.

Figure 2:
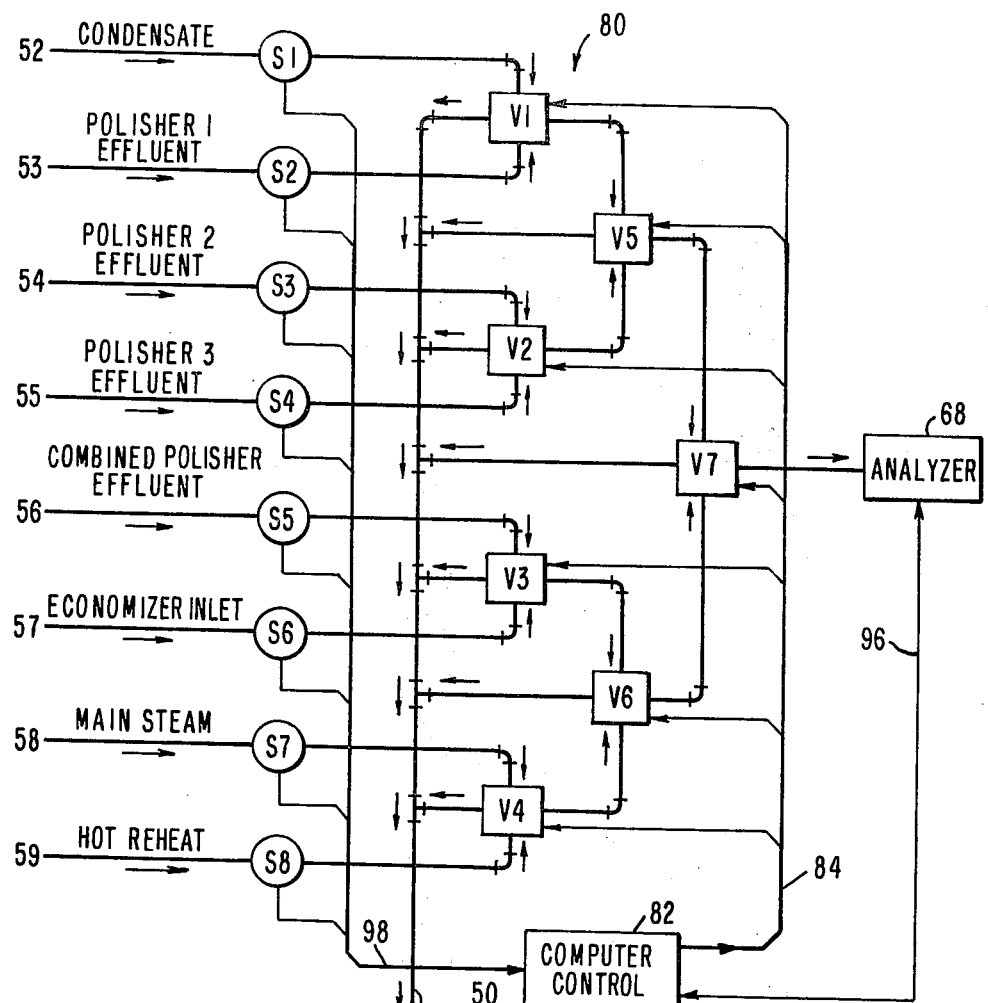
FIG. 2 is a block diagram illustrating one embodiment of the present invention.

The sampling system 50 is illustrated in more detail in FIG. 2 and includes a valve arrangement 80 having a plurality of valves V1–V7 each of which governs fluid flow therethrough in response to an applied control signal. Such control signals are provided by a control 82 in the form of a digital computer having a set of stored instructions for generating output control signals applied to the individual valves by means of control lines 84.

Figure 3A:
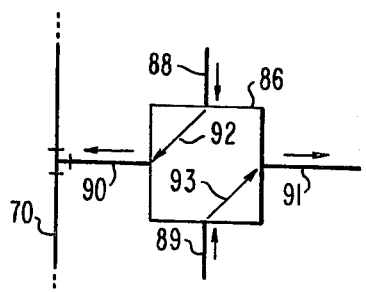
FIGS. 3A and 3B illustrate the fluid flow through a typical valve of FIG. 2.
Figure 3B:
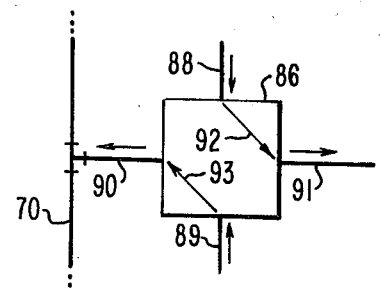

The valves are of the type through which there is a continuous flow of fluid, as opposed to a simple on/off type of valve. For example, FIGS. 3A and 3B illustrate the fluid flow through a typical valve which may be utilized herein. In FIGS. 3A and 3B block 86 represents the valve body, lines 88 and 89 are input lines to the valve whereas lines 90 and 91 are output lines there-from. Arrows 92 and 93 represent the fluid flow through the valve body. Computer 82 may provide a logical ZERO to selected one of the valves in which case it will assume a fluid flow orientation as in FIG. 3A whereas the provision of a logical ONE from the computer will cause a valve to assume a fluid flow condition as in FIG. 3B. Therefore, to communicate an individual one of the fluid sample lines to the analyzer while communicating the remainder to the common drain line, control signals may be provided in accordance with Table I.

TABLE I

| Select Line | Control Signals to Valves | | | | | | |
|---|---|---|---|---|---|---|---|
| | V1 | V2 | V3 | V4 | V5 | V6 | V7 |
| 52 | 1 | * | * | * | 1 | * | 1 |
| 53 | 0 | * | * | * | 1 | * | 1 |
| 54 | * | 1 | * | * | 0 | * | 1 |
| 55 | * | 0 | * | * | 0 | * | 1 |
| 56 | * | * | 1 | * | * | 1 | 0 |
| 57 | * | * | 0 | * | * | 1 | 0 |
| 58 | * | * | * | 1 | * | 0 | 0 |
| 59 | * | * | * | 0 | * | 0 | 0 |

*can be either 1 or 0

Although the valve arrangement 80 includes one less valve than lines to be sampled, other arrangements are possible. For example, each line may have its own individual valve for communicating that line directly with the analyzer, with the valve being of the type wherein there is continuous fluid flow either to the analyzer, when that line is selected by computer 82, or to the common drain line 70. With the continuous flow feature any particular fluid sample is immediately ready for analysis whereas if the lines were dead ended, that is, connected to a valve which is either fully opened or fully closed, then a great deal of time would be wasted for a sample to be equilibrated. For ultra-high purity water samples as found in the steam turbine environment, this equilibration time may be as high as 24 hours.

Once a line has been selected for sampling in accordance with the stored program in computer 82, analyzer 68 will perform its analysis function as dictated by the computer via link 96. Once the results of the analysis have been obtained the computer will select the next sample line in accordance with its stored instructions or alternatively will examine another sample, out of its normal sequence, in accordance with the results of the analysis as provided to the computer via link 96.

The apparatus of the present invention is additionally designed and constructed to interrupt the predetermined schedule of sampling in response to abnormal conditions in the fluid sample lines. More particularly, a plurality of sensors S1-S8 are provided for respective fluid sample lines 52-59 and are designed to measure some predetermined parameter of the fluid in the fluid sample line. By way of example, such sensors may be conductivity meters which supply respective output signals via signal lines 98 to the computer 82 which functions to continuously scan the sensor outputs, compare each with predetermined stored limits and in the absence of an alarm condition (a reading out of normal limits) the computer will sample each line according to its programmed instructions. When one or more lines reach alarm levels the normal analysis sequence will be interrupted to service the alarm sample. In the case of several alarms a priority basis is utilized for the sampling.

We claim:

1. Apparatus for sampling fluids from a plurality of sampling points in a steam turbine system having a steam supply, a steam turbine arrangement driven thereby, a condenser for condensing exhaust steam from said turbine arrangement and a recirculating fluid path, for returning condensed steam back to said supply, comprising:
    (A) a valve arrangement having a plurality of valves each of which may be activated in response to an applied control signal;
    (B) a plurality of fluid sample lines connected between selected points in said steam turbine system and said valve arrangement;
    (C) analyzing means for analyzing selected fluid samples passed by said valving arrangement;
    (D) a common drain line connected to supply fluid back to said steam turbine system;
    (E) computer means operable to supply said applied control signals control signals to activate selected ones of said valves in accordance with a set of stored instructions, so as to place a single one of said fluid sample lines in fluid communication with said analyzing means;
    (F) said computer means and valve arrangement being such that all non-selected fluid sample lines are in continuous fluid communication with said common drain line so as to return fluid in said sample lines back to said steam turbine system from which it came, for reuse thereby.

2. Apparatus according to claim 1 which includes:
    (A) a plurality of sensors, each in fluid communication with a selected one of said fluid sample lines and each operable to provide an output signal indicative of a predetermined condition of the fluid in its associated line;
    (B) said computer means being responsive to said output signals to interrupt the preprogrammed sampling sequence in response to an abnormal one of said output signals.

3. Apparatus according to claim 2 wherein:
    (A) said sensors are conductivity meters.

4. Apparatus according to claim 1 wherein:
    (A) said common drain line is connected to return fluid back to said condenser.

5. Apparatus according to claim 1 which includes:
    (A) means in selected ones of said fluid sample lines operable to reduce the pressure and temperature of a fluid sample taken from said steam turbine system.

6. Apparatus according to claim 1 wherein:
    (A) said computer means is operatively connected to receive the results of said analyzing means and to interrupt the preprogrammed sampling sequence in response to an abnormal analysis.

7. Apparatus according to claim 1 wherein:
    (A) said valves are of the type which includes a minimum of one input and two outputs whereby entering fluid is directed to one output or the other so as to provide for continuous flow through said valve.

* * * * *